(12) United States Patent
Maatta et al.

(10) Patent No.: US 7,915,445 B2
(45) Date of Patent: Mar. 29, 2011

(54) METHOD AND ARRANGEMENT FOR THE PREPARATION OF PERCARBOXYLIC ACID

(75) Inventors: Lauri Maatta, Oulu (FI); Seppo Pohjanvesi, Oulu (FI)

(73) Assignee: Kemira Oyj, Helsinki (FI)

( * ) Notice: Subject to any disclaimer, the term of this patent is extended or adjusted under 35 U.S.C. 154(b) by 435 days.

(21) Appl. No.: 10/494,339

(22) PCT Filed: Apr. 11, 2002

(86) PCT No.: PCT/FI02/00303
§ 371 (c)(1),
(2), (4) Date: Apr. 30, 2004

(87) PCT Pub. No.: WO03/037858
PCT Pub. Date: May 8, 2003

(65) Prior Publication Data
US 2005/0014970 A1    Jan. 20, 2005

(30) Foreign Application Priority Data
Oct. 30, 2001 (FI) .................................. 20012098

(51) Int. Cl.
*C07C 409/24* (2006.01)
(52) U.S. Cl. ............................................... 562/6
(58) Field of Classification Search ............... 562/2, 4, 562/6
See application file for complete search history.

(56) References Cited

U.S. PATENT DOCUMENTS

| | | | | | |
|---|---|---|---|---|---|
| 3,953,298 | A | * | 4/1976 | Hogan | 196/133 |
| 4,135,985 | A | * | 1/1979 | La Rocca | 202/176 |
| 4,141,798 | A | * | 2/1979 | Grosse | 202/234 |
| 4,267,021 | A | * | 5/1981 | Speros et al. | 202/176 |
| 4,487,659 | A | * | 12/1984 | Stark | 202/172 |
| 5,628,879 | A | * | 5/1997 | Woodruff | 202/234 |
| 5,886,216 | A | * | 3/1999 | Pudas | 562/6 |
| 6,171,551 | B1 | * | 1/2001 | Malchesky et al. | 422/29 |
| 6,677,477 | B2 | * | 1/2004 | Pohjanvesi et al. | 562/6 |
| 6,677,478 | B2 | * | 1/2004 | Pohjanvesi et al. | 562/6 |

FOREIGN PATENT DOCUMENTS

| | | | |
|---|---|---|---|
| DE | 3638552 A1 | | 5/1988 |
| EP | 0641777 A1 | | 3/1995 |
| EP | 0 789 016 A1 | | 8/1997 |
| EP | 0974581 | * | 3/1999 |
| EP | 0974581 A1 | | 1/2000 |
| EP | 1004576 A1 | | 5/2000 |
| GB | 1014361 | | 3/1963 |
| WO | WO 94/20424 A1 | | 9/1994 |
| WO | WO 0102596 A1 | | 1/2001 |
| WO | WO 01/10215 A1 | | 2/2001 |

OTHER PUBLICATIONS

Dul'neva et al., Russian Journal of Chemistry, 57, 7, 1125-1130.*
"Peracetic Acid (CAS No. 79-21-0) and its Equilibrium Solutions", ECETOC JACC No. 40, Jan. 31, 2001, pp. 2-3 and 10.
Amini et al., "On-Site Peracids: Tools for Bleaching Strategies to Meet the Cluster Rule and Considerations on Selecting Among Them", Tappi Journal, vol. 78, No. 10, pp. 121-133, Oct. 1995.

* cited by examiner

*Primary Examiner* — Karl J Puttlitz
(74) *Attorney, Agent, or Firm* — Birch, Stewart, Kolasch & Birch, LLP

(57) ABSTRACT

The invention relates to a method and an arrangement in which a percarboxylic acid product is prepared and used. Conventional methods include refrigerated transport and double storage of the percarboxylic acid product before the consumption thereof at its site of use. These expensive stages have now been eliminated carrying out the preparation in connection with the use.

13 Claims, 1 Drawing Sheet

Block diagram of a peracetic acid process according to the invention

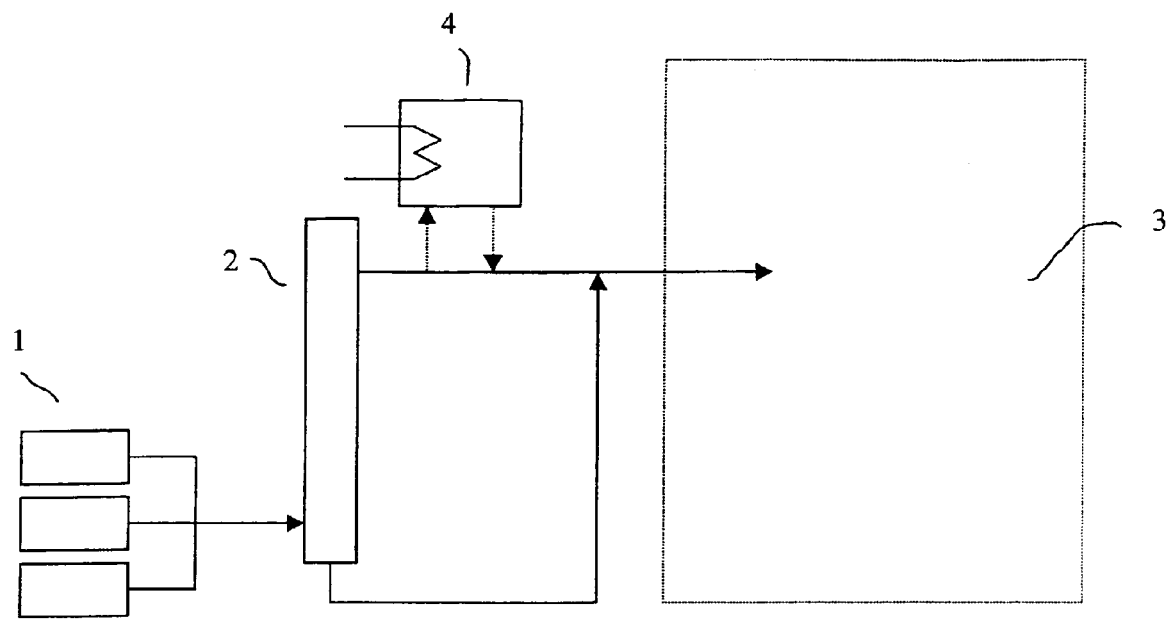
FIGURE
Block diagram of a peracetic acid process according to the invention

METHOD AND ARRANGEMENT FOR THE PREPARATION OF PERCARBOXYLIC ACID

This application is the national phase of PCT International Application No. PCT/FI2002/00303 filed on Apr. 11, 2002, which designated the United States.

FIELD OF THE INVENTION

The invention relates to a method for the preparation of a percarboxylic acid product from its raw materials and using it, whereby the preparation is carried out in connection with the use. The invention also relates to an arrangement comprising means for preparing a percarboxylic acid product and means for using the percarboxylic acid product, wherein the means for preparing the percarboxylic acid product are integrated with the means for using the percarboxylic acid product.

BACKGROUND OF THE INVENTION

Percarboxylic acid, such as peracetic acid and perpropionic acid, are commonly prepared by feeding hydrogen peroxide and acetic or propionic acid continuously to a reaction medium containing hydrogen peroxide, said carboxylic acid and an acid catalyst, wherein the hydrogen peroxide and the acetic acid or propionic acid react and form percarboxylic acid, and by distilling percarboxylic acid concentrated distillate continuously from the reaction medium.

Percarboxylic acids such as peracetic acid and perpropionic acid can be used as bleaching and disinfecting chemicals. Being environmentally friendly, distilled peracetic acid is very suitable as a chemical for the bleaching of chemical pulp. By using peracetic acid, the total selectivity of TCF bleaching can be improved by carrying out acid delignification stages between the alkaline stages. In addition to delignification, the peracetic acid stages also improves the brightness of the pulp, and therefore, it is well suited for the after-bleaching of ECF and TCF pulps.

The disinfective properties of peracetic acid are utilized e.g. for improving the preservation of pigment suspensions, which enables the recirculation of the waste paste in paper mills. The bleaching properties of the peracetic and perpropionic acids can also be utilized for bleaching the pigment suspension used at the paper machine.

In pulp mills and in the bleaching of pigments, large quantities of peracetic acid are needed both in production and full scale trial runs. In the storage and transportation of distilled peracetic acid, the characteristic features of the chemical must be observed. In order to avoid the characteristic decomposition of peroxides ($H_2O_2 \Rightarrow H_2O + \frac{1}{2}O_2$), the product is usually stabilized in connection with the preparation. Furthermore, the storage and transportation of peracetic acid must take place under refrigeration (about $-10°$ C.). At elevated temperatures, the peracetic acid is converted back into its starting materials, whereby an equilibrium mixture of the peracetic acid is formed ($CH_3COOOH + H_2O \Leftrightarrow CH_3COOH + H_2O_2$).

It is generally known to prepare peracetic acid by feeding hydrogen peroxide and acetic acid continuously to an aqueous reaction medium containing hydrogen peroxide, acetic acid, peracetic acid and acid catalyst, in which medium the hydrogen peroxide and the acetic acid react and form peracetic acid, and distilling peracetic acid concentrate continuously from the reaction medium (U.S. Pat. No. 3,264,346, GB 949,094, GB 1,014,361, EP 296 324, EP 789 016 and EP 1 004 576). As peracetic product, distilled peracetic acid and used reaction medium are obtained.

In these known methods, the bottom product, i.e. the used reaction medium, has only been mentioned as a problematic effluent. A process, in which the bottom product is useful as a disinfectant, odour control agent and microbicide, due to an improvement of its composition, resulting in lower sulfuric acid and metal concentrations, is also known (FI 20010706). On the other hand, it has also been shown, that the bottom product and the distilled peracetic acid concentrate can be combined into a new product, if the acid catalyst of the bottom product is neutralized before the mixing (FI 20010705).

WO-A1-94/20424, WO-A1-01/10215, EP-A1-641777 and DE-A1-3638552 all disclose the preparation of percarboxylic acids in situ for disinfective purposes. As was said in EP-A1-641777, page 3, lines 7 to 11, these processes based on equilibrium mixtures containing peracetic acid, which processes are too slow to produce in situ the required amount of percarboxylic acid.

The transportation of peracetic acid is risky and hence temperature control is required. The transportation to distant sites of use would need the use of refrigerated transport equipment. Besides, refrigerated storage has to be used both on the site of production and the site of use. Thus, both refrigerated transport and refrigerated double storage constitute the main problem lying behind the present invention.

SUMMARY OF THE INVENTION

In the field, there is a need for a method of production and use of percarboxylic acids, which can easily be tailored according to the needs of the process operations lying behind it. Especially, a method and apparatus of said type is strived for, the use of which is independent on the distance in time and space between the percarboxylic acid's preparation and use. Specifically, the invention aims at a method and apparatus for the preparation of a percarboxylic acid product and providing it at its site of use, which method lacks the problems of long refrigerated double storage and transportation, as well as the problem of producing percarboxylic acid too slowly.

BRIEF DESCRIPTION OF THE DRAWINGS

FIG. 1 is a block diagram of the method of preparation of peracetic acid in accordance with the present invention.

DETAILED DESCRIPTION OF THE INVENTION

The aforementioned purposes have now been achieved and problems solved by a new method for the preparation and use of a percarboxylic acid product. The method is mainly characterized by what has been stated in the characterizing part of claim 1.

This means that the fast and effective distillation type preparation and the use of a concentrated percarboxylic acid product are integrated both in time and space. By synchronizing effective preparation and use, the need of large refrigerated buffer storage is eliminated. By carrying out the distillation type preparation at or near the site of use, long temperature controlled or even refrigerated transport of the percarboxylic acid is eliminated. By contrast, percarboxylic acid for fast consumption was earlier prepared at one site and used later at another, distant site.

According to one aspect of the present invention, a method is provided, in which both the raw materials of the percarboxylic acid product and the product itself are prepared at said site of use. However, it is preferred that at least a part of the raw materials of the percarboxylic acid product is brought to the site of use and converted there into said percarboxylic acid product.

By percarboxylic acid product is in this connection meant percarboxylic acid or mixtures containing essential amounts thereof.

The present scope of protection includes all methods for the preparation of a percarboxylic acid product at its site of use. Thus, by said site of use is in this context meant a site where an essential conversion, refining, processing, mixing, treatment or working up of the percarboxylic acid, as well as the use thereof, such as bleaching and disinfection, takes place. Typically, the site of (preparation and) use means a place where the above listed measures take place and which is situated at a distance from the site of raw material production or storage, especially at a transport distance from the site of hydrogen peroxide and/or carboxylic acid production or storage.

Usually, the raw materials comprise hydrogen peroxide, a carboxylic acid, an acid catalyst, optionally a stabilizer, and water. Preferably, the carboxylic acid is propionic acid or acetic acid, most preferably acetic acid. The acid catalyst is typically phosphoric or sulfuric acid, preferably sulfuric acid. The stabilizer is e.g. dipicolinic acid. The reaction medium of a continuous process is formed when a certain steady state or equilibrium is reached between the composition of the feed, the composition of the reaction medium, and the composition of the distillate.

Normally, in the invention, the hydrogen peroxide and the carboxylic acid are both brought to the site of use. According to a first embodiment, the hydrogen peroxide, the carboxylic acid and the aqueous acid catalyst are brought separately to said site.

According to a second embodiment, the hydrogen peroxide and the carboxylic acid are brought to the site of use in the form of a mixture and the aqueous catalyst is brought to said site separately from the mixture. In that case, the hydrogen peroxide and the carboxylic acid are preferably brought to said site in the form of an equilibrium mixture.

According to a third embodiment, the hydrogen peroxide, the aqueous catalyst, and preferably, a stabilizer, are brought to the site of use in the form of a mixture, and the carboxylic acid is brought to said site separately from the mixture. The same applies for the feeding of the raw materials to the reaction mixture.

According to a fourth embodiment, the hydrogen peroxide, the carboxylic acid, the aqueous catalyst and an optional stabilizer are brought to said site in the form of a stable reaction mixture. The preparation then begins by distilling of the equilibrium amount of percarboxylic acid and adding the corresponding amount of hydrogen peroxide and carboxylic acid.

The water raw material may be included into any of the above mentioned feed portions. Preferably, the acid catalyst portion always contains water.

In addition to the above mentioned raw materials, at least a part of the apparatus for preparing the percarboxylic acid product is preferably brought to the site of use. For more details, see the description of such a mobile and/or transportable apparatus below.

At the site of use, the hydrogen peroxide and the carboxylic acid are reacted to form percarboxylic acid. Preferably, at the site of use, the hydrogen peroxide and the carboxylic acid are fed continuously to a reaction medium containing said aqueous solution of the acid catalyst where they are mixed, react and form a reaction mixture containing said percarboxylic acid. The carboxylic acid concentration of the reaction medium is preferably kept between 10 and 40% by weight, most preferably between 20 and 30% by weight. The molar ratio between the hydrogen peroxide and the carboxylic acid is preferably kept between 0.5:1 and 5:1, most preferably at about 1:1.

At the site of use, the formed percarboxylic acid is typically distilled off continuously in the form of a percarboxylic acid concentrate, which constitutes at least a part of said percarboxylic acid product. Preferably, the distillation is carried out so that the distilled concentrate contains from 20 to 70% by weight, more preferably from 30 to 60% by weight, most preferably from 35 to 50% by weight of the percarboxylic acid.

When using the on-site process of the invention, it is possible to recycle the distilled percarboxylic acid concentrate to the raw material feed. This may be convenient e.g. during a production stop.

According to one embodiment of the invention, at the site of use, the acid catalyst is continuously fed to the reaction medium and a part of the reaction medium is continuously removed, preferably forming a part of said percarboxylic acid product. Thereby, it is preferred, that 3 to 5% by weight of the reaction medium is continuously removed. The acid catalyst concentration is advantageously kept at a level, the pH of which corresponds to 0.5 to 10% by weight, preferably 1 to 5% by weight, most preferably 2 to 3% by weight, of sulfuric acid.

According to another embodiment of the invention, at the site of use, at least part of the distilled percarboxylic acid concentrate is mixed with the removed part of the reaction medium (as bottom product) to form at least a part of said reaction product. In that case, the acid catalyst present is preferably neutralized, giving a more useful percarboxylic acid product. See above, where FI 20010705 is referred to.

Although the invention has made possible the synchronization of effective percarboxylic acid preparation and use, the raw materials and the percarboxylic acid are not always immediately consumed at the site of use. Therefore, according to one embodiment of the invention, at least part of the raw materials is stored at said site in order to buffer the received and converted amounts of raw material. Correspondingly, at least part of the percarboxylic acid product may also be stored at said site in order to buffer the converted and used amounts of the percarboxylic acid product.

As was mentioned earlier, the percarboxylic acid product is typically used for bleaching and/or disinfection. Therefore, the preparation preferably takes place in connection with the bleaching and/or disinfection. Correspondingly, said site of use is typically the site of bleaching and/or disinfection. As a result of the process integration of the invention, it is possible to add functional compounds to the percarboxylic acid product according to the estimated consumption. Thus, when using the on-site prepared percarboxylic acid product for bleaching, a complex forming agent may be added in controlled amounts to said product.

In addition to the above described method, the invention also relates to an arrangement comprising means for preparing effectively a percarboxylic acid product and means for using the percarboxylic acid product. It was found, that in most cases, a specific arrangement is needed to solve the above-identified problem related to refrigerated storage and transport of percarboxylic acid products in connection to their use.

In the claimed arrangement the means for preparing the percarboxylic acid product are integrated with the means for using the percarboxylic acid product. Thus, by the arrangement or combination of the means for the preparation and use of the percarboxylic acid product, a more complete, harmonious and coordinated entity has been formed.

The claimed arrangement is characterized in that the means for preparing the percarboxylic acid product comprise a reaction vessel for the conversion of the raw materials into the percarboxylic acid, and a distillation column for distilling off the formed percarboxylic acid in the form of a percarboxylic acid concentrate.

Preferably, the integrated means of the claimed installation comprises mobile and/or transportable means for the conversion of raw materials into the percarboxylic acid product at the site of use. Preferably, it also comprises means for the transportation of at least part of the percarboxylic acid raw materials to the site of use. The meaning of the expression "the site of use" has been explained above in connection with the claimed method.

Like in the claimed method described above, the raw materials typically comprise hydrogen peroxide, a carboxylic acid, an acid catalyst, optionally a stabilizer, and water. The carboxylic acid is typically propionic acid or acetic acid, preferably acetic acid and, independently, the acid catalyst is typically phosphoric acid or sulfuric acid preferably sulfuric acid. A typical stabilizer is dipicolinic acid.

Preferably, the means for the transportation of at least part of the raw materials to the site of use comprise at least one tank or vessel and a transport vehicle.

Within the present scope of protection, only part of the raw material may be brought to the site of use. Usually, almost all industrial sites have water, in which case water need not be brought to the site of use, unless it is used for the dilution of, and therefore transported with, the acid catalyst. Further, if the percarboxylic acid is used in the pulping industry, which can produce acetic acid as a by product, it may not be necessary to bring acetic acid to the site of use. Other pulping mills may have hydrogen peroxide production, in which case only the acetic acid is brought to the site of use according to the invention.

According to a first embodiment, the means for the transportation of at least part of the raw materials to the site of use comprises a separate tank or vessel for the hydrogen peroxide and a separate tank or vessel for the carboxylic acid.

According to a second embodiment, the means for the transportation of at least part of the raw materials to the site of use comprises a tank or vessel for a mixture of the hydrogen peroxide and the carboxylic acid. In this case, a separate tank or vessel exists for a solution of the acid catalyst in at least part of the water raw material. This tank is separate from the tank or vessel for the mixture, since otherwise, unacceptable amounts of percarboxylic acid may be prematurely formed.

According to a third embodiment, the means for the transportation of at least part of the raw materials to the site of use comprises a separate tank or vessel for a mixture of the hydrogen peroxide, the acid catalyst and preferably the stabilizer and a separate tank for the acetic acid.

The mobile and/or transportable means for the conversion of the raw materials into the percarboxylic acid product at the site of use typically comprises feed vessels for the raw materials, a reaction vessel for the conversion of the raw materials into the percarboxylic acid, and a distillation column for distilling off the formed percarboxylic acid in the form of a percarboxylic acid concentrate.

The feed tanks may correspond to the transportation tanks or vessels in connection with the three embodiments described above. Typically, there are three tanks for feeding the raw materials into the reaction vessel, namely, one for the hydrogen peroxide, which usually is in the form of an aqueous solution, one for the acetic acid, and one for the water, which usually also contains the acid catalyst and optionally a stabilizer.

Typically, the means for the conversion of the raw materials into the percarboxylic acid product at the site of use are equipped with means for achieving a continuous process.

Preferably, the distillation column is arranged to produce a percarboxylic acid concentrate containing from 20 to 70% by weight, preferably from 30 to 60% by weight, most preferably from 35 to 50% by weight of the percarboxylic acid.

According to a further embodiment of the invention, said mobile and/or transportable means has further means for continuously adding acid catalyst to the reaction medium formed by the raw materials and means for continuously removing and recovering a part of the reaction medium.

It is also preferred, if said mobile and/or transportable means has further means for mixing said part of the reaction medium with said distilled percarboxylic acid concentrate.

Further, the arrangement according to the invention preferably comprises containers for packaging said mobile and/or transportable means for the conversion of the raw materials into the percarboxylic acid product.

Still further, the arrangement according to the invention preferably comprises tanks or vessels for buffering the received and converted amounts of raw materials and tanks or vessels for buffering the converted and used amounts of the percarboxylic acid product.

The capacity of the mobile and/or transportable on-site unit according to the invention is mainly dependent on the transportation restrictions and facilities. The capacity of permanent on-site units may be from hundreds to thousands of tons 100% percarboxylic acid per annum.

In the following, the invention will be described in more detail by referring to FIG. 1, which shows a block diagram of the method according to the invention for the preparation of peracetic acid.

In the case of peracetic acid, acetic acid, hydrogen peroxide, acid catalyst, stabilizer and water are used as raw materials. The used acid catalyst is sulfuric acid and the used stabilizer is dipicolinic acid. The raw materials are transported in a transporting vessel to the feeding tanks 1 of the on-site factory, which feeding tanks are usually three; one for the hydrogen peroxide, one for the acetic acid and one for the water. The water tank usually also contains the acid catalyst and a stabilizer for the peracetic acid.

The distillation column 2 including its operating device is located in a transportable container, which is raised vertically at the site of use. The hydrogen peroxide, the acetic acid, the water and the sulfuric acid catalyst are fed to the bottom of the distillation column 2 (also called reactor). The formed solution is diluted with water so that the leaving distillate has the right concentration. The amount of sulfuric acid added to the bottom of the distillation column is the same as that which is removed together with a part of the reaction medium. The column uses under pressure and a temperature of about 45 to 55° C. The raw materials react at the bottom of the column forming peracetic acid and water.

From the so formed equilibrium solution, the peracetic acid is distilled together with some water out through the upper end of the distillation column. From 3 to 5% by weight, based on the amount of the equilibrium solution (the reaction medium), is removed as bottom product. To the raw material feed, new sulfuric acid corresponding to the amount of removed sulfuric acid is added with the purpose of keeping its concentration correctly at 1-5% by weight. The bottom product contains from 10 to 15% by weight of peracetic acid, about 25% by weight of acetic acid, about 20% by weight of hydrogen peroxide, and about 3% by weight of sulfuric acid. The product (distillate) contains about 40% by weight of peracetic acid, below 4% by weight of acetic acid and below 2% by weight of hydrogen peroxide. The product is conducted straight to the process of use 3 or to the refrigerated buffer storage vessel 4.

Deviating from the embodiment according to the FIGURE, in which the bottom product is mixed with the distillate, the bottom product can be used entirely or partly for the treatment of the operation process waste such as for the disinfection of waste water or the treatment of the waste paste.

With respect to the transportation of the raw materials, it is also possible to mix the hydrogen peroxide and the acetic acid into a mixture before their transport, whereby they form an equilibrium mixture. The equilibrium mixture is stable and it can be transported and stored in non-refrigerated transport vessels.

The on-site production method according to the invention offers significant advantages compared to traditional technique. The percarboxylic acid need not be transported. Large refrigerated storage and transport tanks or cisterns are not needed either, at most small buffer tanks. Further, a storage stabilizer is not needed, either. The possibilities to use the bottom product are improved considerably.

The invention claimed is:

1. A process for the preparation of a percarboxylic acid product from its raw materials at its site of use for bleaching and disinfection, the raw materials comprising a carboxylic acid, hydrogen peroxide, water and an acid catalyst, comprising the steps of:
   i) mixing the carboxylic acid and the hydrogen peroxide into an equilibrium mixture containing the carboxylic acid and the hydrogen peroxide in equilibrium with percarboxylic acid and water;
   ii) bringing the equilibrium mixture to said site of use;
   iii) bringing a mobile distillation column and its operating device to the site of use;
   iv) feeding the equilibrium mixture, the water and the acid catalyst to the bottom of the mobile distillation column; and
   v) separating and recovering the percarboxylic acid product by distillation from the upper end of the mobile distillation column,
wherein from hundreds to thousands of tons of percarboxylic acid product are produced per annum at the site of use.

2. A process for the preparation of a percarboxylic acid product, comprising:
   i) continuously feeding a raw material feed comprising hydrogen peroxide and carboxylic acid to a reaction medium;
   ii) mixing the carboxylic acid and the hydrogen peroxide into an equilibrium mixture containing the carboxylic acid and the hydrogen peroxide in equilibrium with percarboxylic acid and water;
   iii) bringing the equilibrium mixture to a site of use;
   iv) feeding the equilibrium mixture, water and an acid catalyst to the bottom of a distillation column; and
   v) separating and recovering the percarboxylic acid product by distillation from the upper end of the distillation column.

3. The process according to claim 2, wherein the percarboxylic acid product is distilled off continuously in the form of a percarboxylic acid concentrate.

4. The process according to claim 3, wherein the percarboxylic acid product contains from 20 to 70% by weight of percarboxylic acid.

5. The process according to claim 4, wherein the percarboxylic acid product contains from 30 to 60% by weight of percarboxylic acid.

6. The process according to claim 5, wherein the percarboxylic acid product contains from 35 to 50% by weight of percarboxylic acid.

7. The process according to claim 3, wherein a part of the distilled percarboxylic acid concentrate is recycled to the raw material feed.

8. The process according to claim 2, wherein about 40% by weight of peracetic acid, less than 4% by weight of acetic acid and less than 2% by weight of hydrogen peroxide are recovered from the upper end of the distillation column in step v).

9. The process according to claim 8, further comprising:
   vi) removing a bottom product from the bottom of the distillation column,
   wherein the bottom product comprises from 10 to 15% by weight of peracetic acid, about 25% by weight of acetic acid, and about 20% by weight of hydrogen peroxide.

10. A process for the preparation of peracetic acid at its site of use, comprising:
    i) continuously feeding a raw material feed comprising hydrogen peroxide and carboxylic acid to a reaction medium;
    ii) mixing the carboxylic acid and the hydrogen peroxide into an equilibrium mixture containing the carboxylic acid and the hydrogen peroxide in equilibrium with percarboxylic acid and water;
    iii) bringing the equilibrium mixture to a site of use;
    iv) feeding the equilibrium mixture, water and an acid catalyst to the bottom of a distillation column;
    v) separating and recovering the percarboxylic acid product by distillation from the upper end of the distillation column; and
    vi) removing a bottom product from the bottom of the distillation column, wherein the bottom product comprises from 10 to 15% by weight of peracetic acid, about 25% by weight of acetic acid, and about 20% by weight of hydrogen peroxide.

11. The process according to claim 1, wherein the acid catalyst is brought to the site of use separately from the hydrogen peroxide and the carboxylic acid as an aqueous solution formed with said water.

12. The process according to claim 11, wherein the hydrogen peroxide and the carboxylic acid are brought to the site of use as a stable mixture containing the acid catalyst.

13. The process according to claim 1, wherein at least part of the percarboxylic acid product is stored at the site of use in order to buffer the converted and used amounts of the percarboxylic acid product.

* * * * *